(12) United States Patent
Govari et al.

(10) Patent No.: US 12,419,683 B2
(45) Date of Patent: Sep. 23, 2025

(54) IRREVERSIBLE ELECTROPORATION WITH SHORTED ELECTRODES

(71) Applicant: Biosense Webster (Israel) Ltd., Yokneam (IL)

(72) Inventors: Assaf Govari, Haifa (IL); Christopher Thomas Beeckler, Brea, CA (US); Joseph Thomas Keyes, Sierra Madre, CA (US); Justin George Lichter, Irvine, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 753 days.

(21) Appl. No.: 17/559,558

(22) Filed: Dec. 22, 2021

(65) Prior Publication Data

US 2023/0190363 A1 Jun. 22, 2023

(51) Int. Cl.
*A61B 18/12* (2006.01)
*A61B 18/14* (2006.01)
*A61B 18/00* (2006.01)

(52) U.S. Cl.
CPC ...... *A61B 18/1492* (2013.01); *A61B 18/1206* (2013.01); *A61B 2018/00267* (2013.01); *A61B 2018/00351* (2013.01); *A61B 2018/00613* (2013.01); *A61B 2018/00767* (2013.01); *A61B 2018/00916* (2013.01); *A61B 2018/1475* (2013.01)

(58) Field of Classification Search
CPC .. A61B 18/1492; A61B 18/1206–1293; A61B 2018/00613; A61B 2018/00267; A61B 2018/0016; A61B 2018/1467; A61B 2018/00351–00392
See application file for complete search history.

(56) References Cited

U.S. PATENT DOCUMENTS 4,699,147 A 10/1987 Chilson et al.
4,940,064 A 7/1990 Desai
(Continued)

FOREIGN PATENT DOCUMENTS

CN 111248993 A 6/2020
CN 111248996 A 6/2020
(Continued)

OTHER PUBLICATIONS

Extended European Search Report dated May 19, 2023, from corresponding EP Application No. 22215386.8.
(Continued)

*Primary Examiner* — Linda C Dvorak
*Assistant Examiner* — Davina E. Lee

(57) ABSTRACT

A system for use with multiple electrodes coupled to respective spines of a probe includes multiple switches connected to the electrodes and configured to short different respective first subsets of the electrodes to each other and different respective second subsets of the electrodes to each other per different respective settings of the switches. The system further includes a processor configured to control the switches so as to alternate through the settings and, for each of the settings, cause a power generator to apply a voltage between the shorted first subset and the shorted second subset while the probe is deployed within a body of a subject. Other examples are also described.

20 Claims, 4 Drawing Sheets

(56) References Cited

U.S. PATENT DOCUMENTS

| | | | |
|---|---|---|---|
| 5,215,103 A | 6/1993 | Desai | |
| 5,255,679 A | 10/1993 | Imran | |
| 5,293,869 A | 3/1994 | Edwards et al. | |
| 5,309,910 A | 5/1994 | Edwards et al. | |
| 5,313,943 A | 5/1994 | Houser et al. | |
| 5,324,284 A | 6/1994 | Imran | |
| 5,345,936 A | 9/1994 | Pomeranz et al. | |
| 5,365,926 A | 11/1994 | Desai | |
| 5,391,199 A | 2/1995 | Ben-Haim | |
| 5,396,887 A | 3/1995 | Imran | |
| 5,400,783 A | 3/1995 | Pomeranz et al. | |
| 5,411,025 A | 5/1995 | Webster, Jr. | |
| 5,415,166 A | 5/1995 | Imran | |
| 5,443,489 A | 8/1995 | Ben-Haim | |
| 5,456,254 A | 10/1995 | Pietroski et al. | |
| 5,465,717 A | 11/1995 | Imran et al. | |
| 5,476,495 A | 12/1995 | Kordis et al. | |
| 5,499,981 A | 3/1996 | Kordis | |
| 5,526,810 A | 6/1996 | Wang | |
| 5,546,940 A | 8/1996 | Panescu et al. | |
| 5,549,108 A | 8/1996 | Edwards et al. | |
| 5,558,073 A | 9/1996 | Pomeranz et al. | |
| 5,558,091 A | 9/1996 | Acker | |
| 5,577,509 A | 11/1996 | Panescu et al. | |
| 5,595,183 A | 1/1997 | Swanson et al. | |
| 5,598,848 A | 2/1997 | Swanson et al. | |
| 5,609,157 A | 3/1997 | Panescu et al. | |
| 5,628,313 A | 5/1997 | Webster, Jr. | |
| 5,681,280 A | 10/1997 | Rusk et al. | |
| 5,722,401 A | 3/1998 | Pietroski et al. | |
| 5,722,403 A | 3/1998 | McGee et al. | |
| 5,725,525 A | 3/1998 | Kordis | |
| 5,730,128 A | 3/1998 | Pomeranz et al. | |
| 5,772,590 A | 6/1998 | Webster, Jr. | |
| 5,782,239 A | 7/1998 | Webster, Jr. | |
| 5,782,899 A | 7/1998 | Imran | |
| 5,823,189 A | 10/1998 | Kordis | |
| 5,881,727 A | 3/1999 | Edwards | |
| 5,893,847 A | 4/1999 | Kordis | |
| 5,904,680 A | 5/1999 | Kordis et al. | |
| 5,911,739 A | 6/1999 | Kordis et al. | |
| 5,928,228 A | 7/1999 | Kordis et al. | |
| 5,944,022 A | 8/1999 | Nardella et al. | |
| 5,968,040 A | 10/1999 | Swanson et al. | |
| 5,983,126 A | 11/1999 | Wittkampf | |
| 6,014,579 A | 1/2000 | Pomeranz et al. | |
| 6,014,590 A | 1/2000 | Whayne et al. | |
| 6,119,030 A | 9/2000 | Morency | |
| 6,177,792 B1 | 1/2001 | Govari et al. | |
| 6,216,043 B1 | 4/2001 | Swanson et al. | |
| 6,216,044 B1 | 4/2001 | Kordis | |
| 6,428,537 B1 | 8/2002 | Swanson et al. | |
| 6,456,864 B1 | 9/2002 | Swanson et al. | |
| 6,574,492 B1 | 6/2003 | Ben-Haim et al. | |
| 6,584,345 B2 | 6/2003 | Govari | |
| 6,600,948 B2 | 7/2003 | Ben-Haim et al. | |
| 6,690,963 B2 | 2/2004 | Ben-Haim et al. | |
| 6,738,655 B1 | 5/2004 | Sen et al. | |
| 6,741,878 B2 | 5/2004 | Fuimaono et al. | |
| 6,748,255 B2 | 6/2004 | Fuimaono et al. | |
| 6,780,183 B2 | 8/2004 | Jimenez, Jr. et al. | |
| 6,788,967 B2 | 9/2004 | Ben-Haim et al. | |
| 6,837,886 B2 | 1/2005 | Collins et al. | |
| 6,866,662 B2 | 3/2005 | Fuimaono et al. | |
| 6,892,091 B1 | 5/2005 | Ben-Haim et al. | |
| 6,970,730 B2 | 11/2005 | Fuimaono et al. | |
| 6,973,340 B2 | 12/2005 | Fuimaono et al. | |
| 6,980,858 B2 | 12/2005 | Fuimaono et al. | |
| 7,048,734 B1 | 5/2006 | Fleischman et al. | |
| 7,149,563 B2 | 12/2006 | Fuimaono et al. | |
| 7,255,695 B2 | 8/2007 | Falwell et al. | |
| 7,257,434 B2 | 8/2007 | Fuimaono et al. | |
| 7,399,299 B2 | 7/2008 | Daniel et al. | |
| 7,410,486 B2 | 8/2008 | Fuimaono et al. | |
| 7,507,234 B2 | 3/2009 | Utley et al. | |
| 7,522,950 B2 | 4/2009 | Fuimaono et al. | |
| 7,536,218 B2 | 5/2009 | Govari | |
| RE41,334 E | 5/2010 | Beatty et al. | |
| 7,846,157 B2 | 12/2010 | Kozel | |
| 7,930,018 B2 | 4/2011 | Harlev et al. | |
| 8,007,495 B2 | 8/2011 | McDaniel et al. | |
| 8,048,063 B2 | 11/2011 | Aeby et al. | |
| 8,103,327 B2 | 1/2012 | Harlev et al. | |
| 8,167,845 B2 | 5/2012 | Wang et al. | |
| 8,224,416 B2 | 7/2012 | De La Rama et al. | |
| 8,235,988 B2 | 8/2012 | Davis et al. | |
| 8,346,339 B2 | 1/2013 | Kordis et al. | |
| 8,435,232 B2 | 5/2013 | Aeby et al. | |
| 8,447,377 B2 | 5/2013 | Harlev et al. | |
| 8,456,182 B2 | 6/2013 | Bar-Tal et al. | |
| 8,498,686 B2 | 7/2013 | Grunewald | |
| 8,517,999 B2 | 8/2013 | Pappone et al. | |
| 8,545,490 B2 | 10/2013 | Mihajlovic et al. | |
| 8,560,086 B2 | 10/2013 | Just et al. | |
| 8,567,265 B2 | 10/2013 | Aeby et al. | |
| 8,712,550 B2 | 4/2014 | Grunewald | |
| 8,755,861 B2 | 6/2014 | Harlev et al. | |
| 8,825,130 B2 | 9/2014 | Just et al. | |
| 8,906,011 B2 | 12/2014 | Gelbart et al. | |
| 8,945,120 B2 | 2/2015 | McDaniel et al. | |
| 8,979,839 B2 | 3/2015 | De La Rama et al. | |
| 9,037,264 B2 | 5/2015 | Just et al. | |
| 9,131,980 B2 | 9/2015 | Bloom | |
| 9,204,929 B2 | 12/2015 | Solis | |
| 9,277,960 B2 | 3/2016 | Weinkam et al. | |
| 9,314,208 B1 | 4/2016 | Altmann et al. | |
| 9,339,331 B2 | 5/2016 | Tegg et al. | |
| 9,486,282 B2 | 11/2016 | Solis | |
| 9,554,718 B2 | 1/2017 | Bar-Tal et al. | |
| D782,686 S | 3/2017 | Werneth et al. | |
| 9,585,588 B2 | 3/2017 | Marecki et al. | |
| 9,597,036 B2 | 3/2017 | Aeby et al. | |
| 9,687,297 B2 | 6/2017 | Just et al. | |
| 9,693,733 B2 | 7/2017 | Altmann et al. | |
| 9,782,099 B2 | 10/2017 | Williams et al. | |
| 9,788,895 B2 | 10/2017 | Solis | |
| 9,801,681 B2 | 10/2017 | Laske et al. | |
| 9,814,618 B2 | 11/2017 | Nguyen et al. | |
| 9,833,161 B2 | 12/2017 | Govari | |
| 9,894,756 B2 | 2/2018 | Weinkam et al. | |
| 9,895,073 B2 | 2/2018 | Solis | |
| 9,907,609 B2 | 3/2018 | Cao et al. | |
| 9,974,460 B2 | 5/2018 | Wu et al. | |
| 9,986,949 B2 | 6/2018 | Govari et al. | |
| 9,993,160 B2 | 6/2018 | Salvestro et al. | |
| 10,014,607 B1 | 7/2018 | Govari et al. | |
| 10,028,376 B2 | 7/2018 | Weinkam et al. | |
| 10,034,637 B2 | 7/2018 | Harlev et al. | |
| 10,039,494 B2 | 8/2018 | Altmann et al. | |
| 10,045,707 B2 | 8/2018 | Govari | |
| 10,078,713 B2 | 9/2018 | Auerbach et al. | |
| 10,111,623 B2 | 10/2018 | Jung et al. | |
| 10,130,420 B2 | 11/2018 | Basu et al. | |
| 10,130,423 B1 * | 11/2018 | Viswanathan | A61B 18/1492 |
| 10,136,828 B2 | 11/2018 | Houben et al. | |
| 10,143,394 B2 | 12/2018 | Solis | |
| 10,172,536 B2 | 1/2019 | Maskara et al. | |
| 10,182,762 B2 | 1/2019 | Just et al. | |
| 10,194,818 B2 | 2/2019 | Williams et al. | |
| 10,201,311 B2 | 2/2019 | Chou et al. | |
| 10,219,860 B2 | 3/2019 | Harlev et al. | |
| 10,219,861 B2 | 3/2019 | Just et al. | |
| 10,231,328 B2 | 3/2019 | Weinkam et al. | |
| 10,238,309 B2 | 3/2019 | Bar-Tal et al. | |
| 10,278,590 B2 | 5/2019 | Salvestro et al. | |
| D851,774 S | 6/2019 | Werneth et al. | |
| 10,314,505 B2 | 6/2019 | Williams et al. | |
| 10,314,507 B2 | 6/2019 | Govari et al. | |
| 10,314,648 B2 | 6/2019 | Ge et al. | |
| 10,314,649 B2 | 6/2019 | Bakos et al. | |
| 10,349,855 B2 | 7/2019 | Zeidan et al. | |
| 10,350,003 B2 | 7/2019 | Weinkam et al. | |
| 10,362,991 B2 | 7/2019 | Tran et al. | |
| 10,375,827 B2 | 8/2019 | Weinkam et al. | |

(56) References Cited

U.S. PATENT DOCUMENTS

| | | | |
|---|---|---|---|
| 10,376,170 B2 | 8/2019 | Quinn et al. |
| 10,376,221 B2 | 8/2019 | Iyun et al. |
| 10,398,348 B2 | 9/2019 | Osadchy et al. |
| 10,403,053 B2 | 9/2019 | Katz et al. |
| 10,441,188 B2 | 10/2019 | Katz et al. |
| 10,470,682 B2 | 11/2019 | Deno et al. |
| 10,470,714 B2 | 11/2019 | Altmann et al. |
| 10,482,198 B2 | 11/2019 | Auerbach et al. |
| 10,492,857 B2 | 12/2019 | Guggenberger et al. |
| 10,542,620 B2 | 1/2020 | Weinkam et al. |
| 10,575,743 B2 | 3/2020 | Basu et al. |
| 10,575,745 B2 | 3/2020 | Solis |
| 10,582,871 B2 | 3/2020 | Williams et al. |
| 10,582,894 B2 | 3/2020 | Ben Zrihem et al. |
| 10,596,346 B2 | 3/2020 | Aeby et al. |
| 10,602,947 B2 | 3/2020 | Govari et al. |
| 10,617,867 B2 | 4/2020 | Viswanathan et al. |
| 10,660,702 B2 | 5/2020 | Viswanathan et al. |
| 10,667,753 B2 | 6/2020 | Werneth et al. |
| 10,674,929 B2 | 6/2020 | Houben et al. |
| 10,681,805 B2 | 6/2020 | Weinkam et al. |
| 10,682,181 B2 | 6/2020 | Cohen et al. |
| 10,687,892 B2 | 6/2020 | Long et al. |
| 10,702,178 B2 | 7/2020 | Dahlen et al. |
| 10,716,477 B2 | 7/2020 | Salvestro et al. |
| 10,758,304 B2 | 9/2020 | Aujla |
| 10,765,371 B2 | 9/2020 | Hayam et al. |
| 10,772,566 B2 | 9/2020 | Aujila |
| 10,799,281 B2 | 10/2020 | Goertzen et al. |
| 10,842,558 B2 | 11/2020 | Harlev et al. |
| 10,842,561 B2 | 11/2020 | Viswanathan et al. |
| 10,863,914 B2 | 12/2020 | Govari et al. |
| 10,881,376 B2 | 1/2021 | Shemesh et al. |
| 10,898,139 B2 | 1/2021 | Guta et al. |
| 10,905,329 B2 | 2/2021 | Bar-Tal et al. |
| 10,912,484 B2 | 2/2021 | Ziv-Ari et al. |
| 10,918,306 B2 | 2/2021 | Govari et al. |
| 10,939,871 B2 | 3/2021 | Altmann et al. |
| 10,952,795 B2 | 3/2021 | Cohen et al. |
| 10,973,426 B2 | 4/2021 | Williams et al. |
| 10,973,461 B2 | 4/2021 | Baram et al. |
| 10,987,045 B2 | 4/2021 | Basu et al. |
| 11,006,902 B1 | 5/2021 | Bonyak et al. |
| 11,040,208 B1 | 6/2021 | Govari et al. |
| 11,045,628 B2 | 6/2021 | Beeckler et al. |
| 11,051,877 B2 | 7/2021 | Sliwa et al. |
| 11,109,788 B2 | 9/2021 | Rottmann et al. |
| 11,116,435 B2 | 9/2021 | Urman et al. |
| 11,129,574 B2 | 9/2021 | Cohen et al. |
| 11,160,482 B2 | 11/2021 | Solis |
| 11,164,371 B2 | 11/2021 | Yellin et al. |
| 2004/0210121 A1 | 10/2004 | Fuimaono et al. |
| 2006/0009689 A1 | 1/2006 | Fuimaono et al. |
| 2006/0009690 A1 | 1/2006 | Fuimaono et al. |
| 2006/0100669 A1 | 5/2006 | Fuimaono et al. |
| 2006/0259029 A1* | 11/2006 | Utley ............... A61B 18/1485 606/41 |
| 2007/0093806 A1 | 4/2007 | Desai et al. |
| 2007/0276212 A1 | 11/2007 | Fuimaono et al. |
| 2008/0234564 A1 | 9/2008 | Beatty et al. |
| 2011/0118726 A1 | 5/2011 | De La Rama et al. |
| 2011/0160574 A1 | 6/2011 | Harlev et al. |
| 2011/0190625 A1 | 8/2011 | Harlev et al. |
| 2011/0245756 A1 | 10/2011 | Arora et al. |
| 2011/0301597 A1 | 12/2011 | McDaniel et al. |
| 2012/0271140 A1 | 10/2012 | Kordis et al. |
| 2013/0172715 A1 | 7/2013 | Just et al. |
| 2013/0172872 A1 | 7/2013 | Subramaniam et al. |
| 2013/0172883 A1 | 7/2013 | Lopes et al. |
| 2013/0178850 A1 | 7/2013 | Lopes et al. |
| 2013/0190587 A1 | 7/2013 | Lopes et al. |
| 2013/0231659 A1 | 9/2013 | Hill et al. |
| 2013/0296852 A1 | 11/2013 | Madjarov et al. |
| 2014/0025069 A1 | 1/2014 | Willard et al. |
| 2014/0052118 A1 | 2/2014 | Laske et al. |
| 2014/0180147 A1 | 6/2014 | Thakur et al. |
| 2014/0180151 A1 | 6/2014 | Maskara et al. |
| 2014/0180152 A1 | 6/2014 | Maskara et al. |
| 2014/0228663 A1 | 8/2014 | Kordis et al. |
| 2014/0257069 A1 | 9/2014 | Eliason et al. |
| 2014/0276712 A1 | 9/2014 | Mallin et al. |
| 2014/0309512 A1 | 10/2014 | Govari et al. |
| 2015/0011991 A1 | 1/2015 | Buysman et al. |
| 2015/0045863 A1 | 2/2015 | Litscher et al. |
| 2015/0080693 A1 | 3/2015 | Solis |
| 2015/0105770 A1 | 4/2015 | Amit |
| 2015/0119878 A1 | 4/2015 | Heisel et al. |
| 2015/0133919 A1 | 5/2015 | McDaniel et al. |
| 2015/0208942 A1 | 7/2015 | Bar-Tal et al. |
| 2015/0250424 A1 | 9/2015 | Govari et al. |
| 2015/0270634 A1 | 9/2015 | Buesseler et al. |
| 2015/0342532 A1 | 12/2015 | Basu et al. |
| 2016/0081746 A1 | 3/2016 | Solis |
| 2016/0113582 A1 | 4/2016 | Altmann et al. |
| 2016/0113709 A1 | 4/2016 | Maor |
| 2016/0183877 A1 | 6/2016 | Williams et al. |
| 2016/0228023 A1 | 8/2016 | Govari |
| 2016/0228062 A1 | 8/2016 | Altmann et al. |
| 2016/0278853 A1 | 9/2016 | Ogle et al. |
| 2016/0302858 A1 | 10/2016 | Bencini |
| 2016/0338770 A1 | 11/2016 | Bar-Tal et al. |
| 2017/0027638 A1 | 2/2017 | Solis |
| 2017/0065227 A1 | 3/2017 | Marrs et al. |
| 2017/0071543 A1 | 3/2017 | Basu et al. |
| 2017/0071544 A1 | 3/2017 | Basu et al. |
| 2017/0071665 A1 | 3/2017 | Solis |
| 2017/0095173 A1 | 4/2017 | Bar-Tal et al. |
| 2017/0100187 A1 | 4/2017 | Basu et al. |
| 2017/0143227 A1 | 5/2017 | Marecki et al. |
| 2017/0156790 A1 | 6/2017 | Aujla |
| 2017/0172442 A1 | 6/2017 | Govari |
| 2017/0185702 A1 | 6/2017 | Auerbach et al. |
| 2017/0202515 A1 | 7/2017 | Zrihem et al. |
| 2017/0221262 A1 | 8/2017 | Laughner et al. |
| 2017/0224958 A1 | 8/2017 | Cummings et al. |
| 2017/0265812 A1 | 9/2017 | Williams et al. |
| 2017/0281031 A1 | 10/2017 | Houben et al. |
| 2017/0281268 A1 | 10/2017 | Tran et al. |
| 2017/0296125 A1 | 10/2017 | Altmann et al. |
| 2017/0296251 A1 | 10/2017 | Wu et al. |
| 2017/0319139 A1 | 11/2017 | Wu et al. |
| 2017/0347959 A1 | 12/2017 | Guta et al. |
| 2017/0354338 A1 | 12/2017 | Levin et al. |
| 2017/0354339 A1 | 12/2017 | Zeidan et al. |
| 2017/0354364 A1 | 12/2017 | Bar-Tal et al. |
| 2017/0367756 A1* | 12/2017 | Sliwa ............... A61B 5/4836 |
| 2018/0008203 A1 | 1/2018 | Iyun et al. |
| 2018/0028084 A1 | 2/2018 | Williams et al. |
| 2018/0049803 A1 | 2/2018 | Solis |
| 2018/0085064 A1 | 3/2018 | Auerbach et al. |
| 2018/0132749 A1 | 5/2018 | Govari et al. |
| 2018/0137687 A1 | 5/2018 | Katz et al. |
| 2018/0160936 A1 | 6/2018 | Govari et al. |
| 2018/0160978 A1 | 6/2018 | Cohen et al. |
| 2018/0168511 A1 | 6/2018 | Hall et al. |
| 2018/0184982 A1 | 7/2018 | Basu et al. |
| 2018/0192958 A1 | 7/2018 | Wu |
| 2018/0206792 A1 | 7/2018 | Auerbach et al. |
| 2018/0235692 A1 | 8/2018 | Efimov et al. |
| 2018/0249959 A1 | 9/2018 | Osypka |
| 2018/0256109 A1 | 9/2018 | Wu et al. |
| 2018/0279954 A1 | 10/2018 | Hayam et al. |
| 2018/0303414 A1 | 10/2018 | Toth et al. |
| 2018/0310987 A1 | 11/2018 | Altmann et al. |
| 2018/0311497 A1 | 11/2018 | Mswanathan et al. |
| 2018/0338722 A1 | 11/2018 | Altmann et al. |
| 2018/0344188 A1 | 12/2018 | Govari |
| 2018/0344202 A1 | 12/2018 | Bar-Tal et al. |
| 2018/0344251 A1 | 12/2018 | Harlev et al. |
| 2018/0344393 A1 | 12/2018 | Gruba et al. |
| 2018/0360534 A1 | 12/2018 | Teplitsky et al. |
| 2018/0365355 A1 | 12/2018 | Auerbach et al. |
| 2019/0000540 A1 | 1/2019 | Cohen et al. |
| 2019/0008582 A1 | 1/2019 | Govari et al. |

(56) References Cited

U.S. PATENT DOCUMENTS

| | | |
|---|---|---|
| 2019/0015007 A1 | 1/2019 | Rottmann et al. |
| 2019/0030328 A1 | 1/2019 | Stewart et al. |
| 2019/0053708 A1 | 2/2019 | Gliner |
| 2019/0059766 A1 | 2/2019 | Houben et al. |
| 2019/0069950 A1 | 3/2019 | Viswanathan et al. |
| 2019/0069954 A1 | 3/2019 | Cohen et al. |
| 2019/0117111 A1 | 4/2019 | Osadchy et al. |
| 2019/0117303 A1 | 4/2019 | Claude et al. |
| 2019/0117315 A1 | 4/2019 | Keyes et al. |
| 2019/0125439 A1 | 5/2019 | Rohl et al. |
| 2019/0133552 A1 | 5/2019 | Shemesh et al. |
| 2019/0142293 A1 | 5/2019 | Solis |
| 2019/0164633 A1 | 5/2019 | Ingel et al. |
| 2019/0167137 A1 | 6/2019 | Bar-Tal et al. |
| 2019/0167140 A1 | 6/2019 | Williams et al. |
| 2019/0188909 A1 | 6/2019 | Yellin et al. |
| 2019/0201664 A1 | 7/2019 | Govari |
| 2019/0209089 A1 | 7/2019 | Baram et al. |
| 2019/0216346 A1 | 7/2019 | Ghodrati et al. |
| 2019/0216347 A1 | 7/2019 | Ghodrati et al. |
| 2019/0231421 A1 | 8/2019 | Mswanathan et al. |
| 2019/0231423 A1 | 8/2019 | Weinkam et al. |
| 2019/0239811 A1 | 8/2019 | Just et al. |
| 2019/0246935 A1 | 8/2019 | Govari et al. |
| 2019/0298442 A1 | 10/2019 | Ogata et al. |
| 2019/0314083 A1 | 10/2019 | Herrera et al. |
| 2019/0328260 A1 | 10/2019 | Zeidan et al. |
| 2019/0343580 A1 | 11/2019 | Nguyen et al. |
| 2020/0000518 A1 | 1/2020 | Kiernan et al. |
| 2020/0008705 A1 | 1/2020 | Ziv-Ari et al. |
| 2020/0008869 A1 | 1/2020 | Byrd |
| 2020/0009378 A1 | 1/2020 | Stewart et al. |
| 2020/0015890 A1 | 1/2020 | To et al. |
| 2020/0022653 A1 | 1/2020 | Moisa |
| 2020/0029845 A1 | 1/2020 | Baram et al. |
| 2020/0046421 A1 | 2/2020 | Govari |
| 2020/0046423 A1 | 2/2020 | Mswanathan et al. |
| 2020/0060569 A1 | 2/2020 | Tegg |
| 2020/0077959 A1 | 3/2020 | Altmann et al. |
| 2020/0093539 A1 | 3/2020 | Long et al. |
| 2020/0129089 A1 | 4/2020 | Gliner et al. |
| 2020/0129125 A1 | 4/2020 | Govari et al. |
| 2020/0129128 A1 | 4/2020 | Gliner et al. |
| 2020/0179650 A1 | 6/2020 | Beeckler et al. |
| 2020/0196896 A1 | 6/2020 | Solis |
| 2020/0205689 A1 | 7/2020 | Squires et al. |
| 2020/0205690 A1 | 7/2020 | Williams et al. |
| 2020/0205737 A1 | 7/2020 | Beeckler |
| 2020/0205876 A1 | 7/2020 | Govari |
| 2020/0205892 A1 | 7/2020 | Mswanathan et al. |
| 2020/0206461 A1 | 7/2020 | Govari et al. |
| 2020/0206498 A1 | 7/2020 | Arora et al. |
| 2020/0289197 A1 | 9/2020 | Mswanathan et al. |
| 2020/0297234 A1 | 9/2020 | Houben et al. |
| 2020/0297281 A1 | 9/2020 | Basu et al. |
| 2020/0305726 A1 | 10/2020 | Salvestro et al. |
| 2020/0305946 A1 | 10/2020 | DeSimone et al. |
| 2020/0345262 A1 | 11/2020 | Selkee et al. |
| 2020/0397328 A1 | 12/2020 | Altmann et al. |
| 2020/0398048 A1 | 12/2020 | Krimsky et al. |
| 2021/0015549 A1 | 1/2021 | Haghighi-Mood et al. |
| 2021/0022684 A1 | 1/2021 | Govari et al. |
| 2021/0045805 A1 | 2/2021 | Govari et al. |
| 2021/0059549 A1 | 3/2021 | Urman et al. |
| 2021/0059550 A1 | 3/2021 | Urman et al. |
| 2021/0059608 A1 | 3/2021 | Beeckler et al. |
| 2021/0059743 A1 | 3/2021 | Govari |
| 2021/0059747 A1 | 3/2021 | Krans et al. |
| 2021/0077184 A1 | 3/2021 | Basu et al. |
| 2021/0082157 A1 | 3/2021 | Rosenberg et al. |
| 2021/0085200 A1 | 3/2021 | Auerbach et al. |
| 2021/0085204 A1 | 3/2021 | Auerbach et al. |
| 2021/0085215 A1 | 3/2021 | Auerbach et al. |
| 2021/0085387 A1 | 3/2021 | Amit et al. |
| 2021/0093292 A1 | 4/2021 | Baram et al. |
| 2021/0093294 A1 | 4/2021 | Shemesh et al. |
| 2021/0093374 A1 | 4/2021 | Govari et al. |
| 2021/0093377 A1 | 4/2021 | Herrera et al. |
| 2021/0100612 A1 | 4/2021 | Baron et al. |
| 2021/0113822 A1 | 4/2021 | Beeckler et al. |
| 2021/0127999 A1 | 5/2021 | Govari et al. |
| 2021/0128010 A1 | 5/2021 | Govari et al. |
| 2021/0133516 A1 | 5/2021 | Govari et al. |
| 2021/0137587 A1* | 5/2021 | Olson ............... A61B 18/1206 |
| 2021/0145282 A1 | 5/2021 | Bar-Tal et al. |
| 2021/0169421 A1 | 6/2021 | Govari |
| 2021/0169568 A1 | 6/2021 | Govari et al. |
| 2021/0177294 A1 | 6/2021 | Gliner et al. |
| 2021/0177356 A1 | 6/2021 | Gliner et al. |
| 2021/0178166 A1 | 6/2021 | Govari et al. |
| 2021/0186363 A1 | 6/2021 | Gliner et al. |
| 2021/0187241 A1 | 6/2021 | Govari et al. |
| 2021/0196372 A1 | 7/2021 | Altmann et al. |
| 2021/0196394 A1 | 7/2021 | Govari et al. |
| 2021/0212591 A1 | 7/2021 | Govari et al. |
| 2021/0219904 A1 | 7/2021 | Yarnitsky et al. |
| 2021/0278936 A1 | 9/2021 | Katz et al. |
| 2021/0282659 A1 | 9/2021 | Govari et al. |
| 2021/0307815 A1 | 10/2021 | Govari et al. |
| 2021/0308424 A1 | 10/2021 | Beeckler et al. |
| 2021/0338319 A1 | 11/2021 | Govari et al. |

FOREIGN PATENT DOCUMENTS

| | | |
|---|---|---|
| CN | 113100916 A | 7/2021 |
| EP | 0668740 A1 | 8/1995 |
| EP | 0644738 B1 | 3/2000 |
| EP | 0727183 B1 | 11/2002 |
| EP | 0727184 B1 | 12/2002 |
| EP | 2783651 A1 | 10/2014 |
| EP | 2699151 B1 | 11/2015 |
| EP | 2699152 B1 | 11/2015 |
| EP | 2699153 B1 | 12/2015 |
| EP | 2498706 B1 | 4/2016 |
| EP | 2578173 B1 | 6/2017 |
| EP | 3238645 A1 | 11/2017 |
| EP | 2884931 B1 | 1/2018 |
| EP | 2349440 B1 | 8/2019 |
| EP | 3318211 B1 | 12/2019 |
| EP | 3581135 A1 | 12/2019 |
| EP | 2736434 B1 | 2/2020 |
| EP | 3451962 B1 | 3/2020 |
| EP | 3960105 A1 | 3/2022 |
| EP | 3972510 A1 | 3/2022 |
| EP | 3991681 A1 | 5/2022 |
| WO | 9421167 A1 | 9/1994 |
| WO | 9421169 A1 | 9/1994 |
| WO | 9625095 A1 | 8/1996 |
| WO | 9634560 A1 | 11/1996 |
| WO | 0066018 A1 | 11/2000 |
| WO | 0182814 B1 | 5/2002 |
| WO | 2004087249 A2 | 10/2004 |
| WO | 2012100185 A2 | 7/2012 |
| WO | 2013052852 A1 | 4/2013 |
| WO | 2013162884 A1 | 10/2013 |
| WO | 2013173917 A1 | 11/2013 |
| WO | 2013176881 A1 | 11/2013 |
| WO | 2014176205 A1 | 10/2014 |
| WO | 2016019760 A1 | 2/2016 |
| WO | 2016044687 A1 | 3/2016 |
| WO | 2018111600 A1 | 6/2018 |
| WO | 2018191149 A1 | 10/2018 |
| WO | 2019084442 A1 | 5/2019 |
| WO | 2019143960 A1 | 7/2019 |
| WO | 2020026217 A1 | 2/2020 |

(56) References Cited

FOREIGN PATENT DOCUMENTS

| | | |
|---|---|---|
| WO | 2020036886 A1 | 2/2020 |
| WO | 2020206328 A1 | 10/2020 |

OTHER PUBLICATIONS

Extended European Search Report dated Aug. 16, 2023, from corresponding EP Application No. 22215244.9.

* cited by examiner

IRREVERSIBLE ELECTROPORATION WITH SHORTED ELECTRODES

CROSS-REFERENCE TO RELATED APPLICATIONS

The present application is related to another application entitled "Compact basket probe", filed on even date herewith.

FIELD OF THE DISCLOSURE

The present disclosure is related to the diagnosis and treatment of physiological disorders, such as electrophysiological disorders of a heart.

BACKGROUND

U.S. Patent Application Publication 2017/0071544 describes a catheter having a basket-shaped electrode assembly formed from a plurality of spines, each with a plurality of electrodes. The spines are connected at their distal ends and extend through the catheter body to its proximal end. Each spine may be independently controlled, such as by adjusting its longitudinal position relative to the catheter body to causes it to bow outwards to a greater or lesser degree.

U.S. Patent Application Publication 2019/0239811 describes an electrode support structure assembly comprising an electrode support structure including a plurality of spines. Each of the plurality of spines can have a proximal end portion and a distal end portion. The assembly further comprises a first element defining an axis and comprising an outer surface. The outer surface comprises a plurality of slots configured to receive the distal end portion of each of the plurality of spines. The first element is configured such that the distal end portion of each of the plurality of spines may move with respect to each slot. In accordance with some embodiments, the distal end portion of each of the plurality of spines comprises a section configured for engagement with the first element, wherein the section comprises a shoulder.

U.S. Patent Application Publication 2006/0100669 describes a method and system for atrial defibrillation in a patient. The method comprises introducing into the patient a catheter comprising an elongated catheter body having proximal and distal ends and at least one lumen therethrough, and a basket-shaped electrode assembly at the distal end of the catheter body. The electrode assembly has proximal and distal ends and comprises a plurality of spines connected at their proximal and distal ends, each spine comprising an elongated spine electrode along its length. The electrode assembly has an expanded arrangement wherein the spines bow radially outwardly and a collapsed arrangement wherein the spines are arranged generally along the axis of the catheter body. The method further comprises introducing the electrode assembly into the heart of the patient and applying defibrillation energy to the tissue through one or more of the elongated electrodes. The system comprises a catheter as described above in combination with an external defibrillator electrically connected to the catheter.

U.S. Pat. No. 7,507,234 describes methods of accessing and ablating abnormal epithelium tissue in an alimentary canal. The methods can include steps of (i) inserting an operative element into an alimentary canal such that the proximate to a portion of the alimentary canal having tissue to be ablated; and (ii) using the operative element to apply cryogenic ablation to a site of abnormal tissue.

BRIEF DESCRIPTION OF THE DRAWINGS

The present disclosure will be more fully understood from the following detailed description of examples thereof, taken together with the drawings, in which.

DETAILED DESCRIPTION OF EXAMPLES

Overview

A basket probe for electrophysiological procedures typically comprises multiple electrodes coupled to a plurality of collapsible spines.

It is challenging to design a basket probe suitable for IRE. On the one hand, if the electrodes on the basket are too small, the relatively high current density delivered from the electrodes may cause damage to the surrounding tissue. On the other hand, if the electrodes are too large, it may be difficult or impossible to safely deploy the probe inside the body.

To address this challenge, examples of the present disclosure provide a basket probe with smaller electrodes, but decrease the current density delivered from each electrode by shorting multiple electrodes together. In other words, the IRE current is passed between a shorted first group (or "subset") of the electrodes, which typically includes around half the electrodes, and a shorted second group, which typically includes the remaining electrodes. Optionally, the current density may be decreased even further by shorting each group of electrodes to the metallic spine(s) of the basket to which the group is coupled.

Moreover, in some examples, using a plurality of switches, the electrodes are rotated between the two groups. In other words, after a pulse is applied between a first group of electrodes and a second group of electrodes, one or more of the electrodes from the first group are moved to the second, and one or more from the second are moved to the first. Subsequently, another pulse is applied. Any number of further rotations and pulse applications may then be performed. Thus, advantageously, the distribution of current across the tissue is varied, such that the effectiveness of the procedure is increased.

Advantageously, examples of the present disclosure reduce the collapsed profile of the basket even further.

For example, in some examples, each spine comprises a superelastic element covered by a polymeric sleeve; for example, the sleeve may be shrink-wrapped around the superelastic element. The sleeves extend from the distal ends of the superelastic elements and are coupled to a surface of a support element by virtue of being bent proximally, into alignment with the surface, at the distal end of the support element. Advantageously, upon the collapse of the basket, the angle of each of the bends becomes relatively small, such that the basket assumes a relatively small profile.

In other examples, rather than being coupled to a distal support element, the spines form loops that cross over each other at the distal end of the basket. To facilitate a smaller collapsed profile of the basket, at least one of the superelastic elements is uncovered at the distal crossover, such that the total thickness of the distal crossover is relatively small.

System Description

Figure 1:
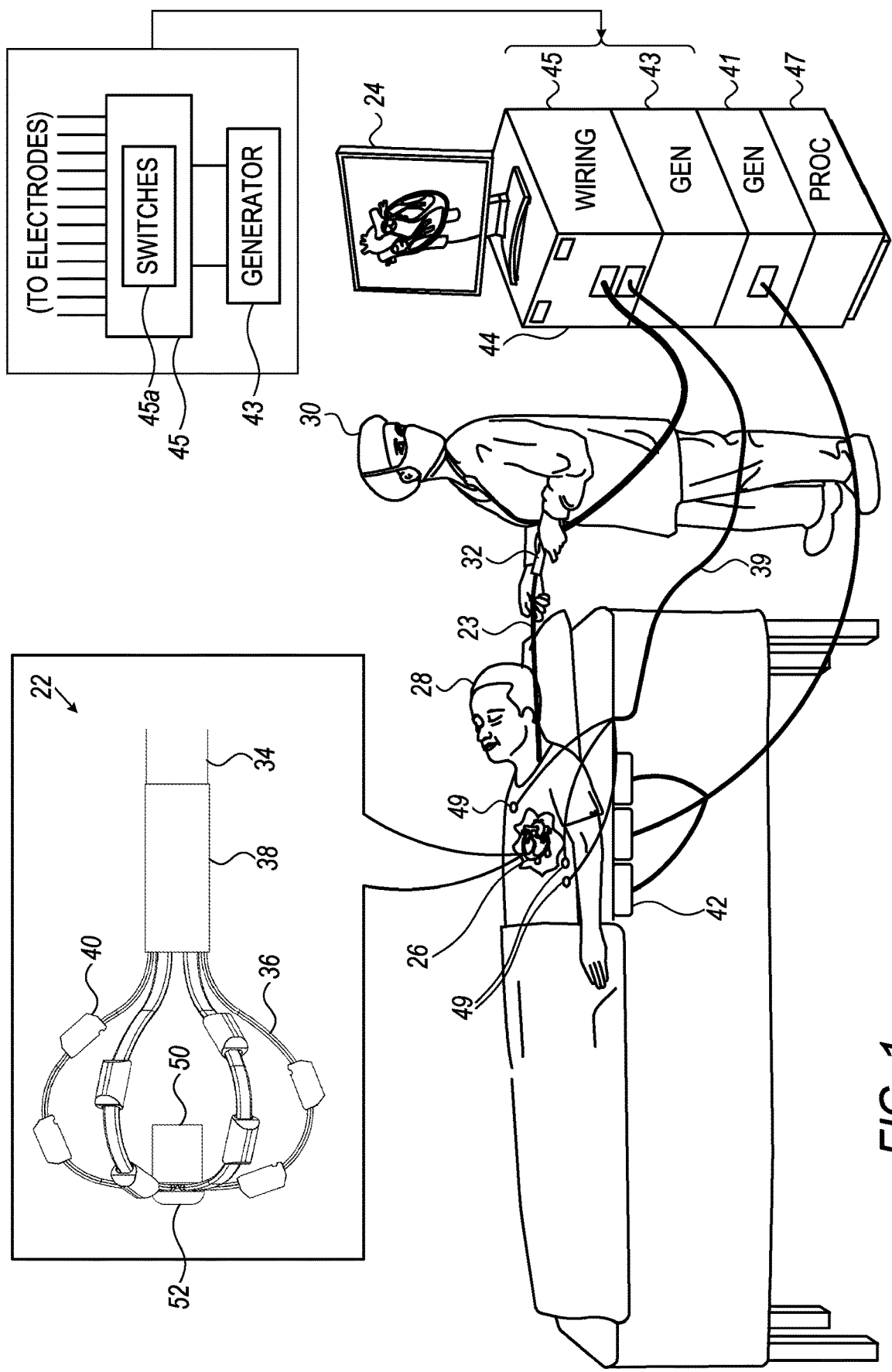
FIG. 1 is a schematic illustration of a system for performing irreversible electroporation (IRE) of tissue of a heart of a subject, in accordance with some examples of the present disclosure.

Reference is initially made to FIG. 1, which is a schematic illustration of a system 20 for performing irreversible electroporation (IRE) of tissue of a heart 26 of a subject 28, in accordance with some examples of the present disclosure.

System 20 comprises an intrabody probe 22, comprising a tube 34 and multiple (e.g., 2-12, such as six) spines 36 proximally coupled to tube 34 at the distal end of probe 22. Spines 36 comprise respective expandable superelastic elements 46 (FIG. 2), typically made of nitinol (e.g., nitinol SE508), configured to expand upon exiting a sheath 23. Probe 22 further comprises multiple electrodes 40 coupled to the spines.

In some examples, a coupling element 38 is coupled to the distal end of tube 34, and spines 36 are coupled to the tube by virtue of being coupled to coupling element 38, e.g., to the inner surface of the coupling element. (In some such examples, coupling element 38 is cylindrical.) In other examples, spines 36 are coupled directly to the tube.

To initiate the IRE procedure, a physician 30 inserts sheath 23 into the body of subject 28, e.g., via the superior or inferior vena cava of the subject. Subsequently, physician 30 navigates the sheath to a chamber of heart 26. Next, the physician deploys probe 22 from the sheath by advancing probe 22 through the sheath, and/or withdrawing the sheath, at least until the spines expand upon exiting the sheath.

System 20 further comprises a power generator (GEN) 43, wiring 45, and a processor 47. Typically, each of these elements is disposed in a console 44.

Wiring 45 is connected to electrodes 40 and is configured to short at least one first subset of electrodes 40 to each other and at least one second subset of the electrodes to each other. Generator 43 is configured to apply a voltage (alternatively referred to herein as a "pulse") between the shorted first subset and the shorted second subset. Typically, to facilitate electroporation of the tissue, the voltage has a constant positive amplitude for at least 100 ns and a constant negative amplitude for at least 100 ns. Typically, the positive amplitude and negative amplitude have the same magnitude; in other words, if the positive amplitude is V, the negative amplitude is -V.

In some examples, the shorting of the first subset and second subset is hardwired by wiring 45. Typically, however, wiring 45 comprises multiple switches 45a having multiple settings per which switches 45a short different respective first subsets of the electrodes to each other and different respective second subsets of the electrodes to each other. Processor 47 is configured to control the switches so as to alternate through the settings and, for each of the settings, cause generator 43 to apply the voltage between the shorted first subset and the shorted second subset.

Thus, following the expansion of the spines, the physician may instruct processor 47 to execute an IRE procedure in which electric currents are passed between the shorted subsets of electrodes 40. To instruct the processor, the physician may manipulate a control mechanism (e.g., a button or switch) on a control handle 32 of the probe, or use any other suitable user interface (e.g., a keyboard, mouse, or touchscreen). In response to the instruction, the processor executes the procedure by controlling generator 43 and (typically) switches 45a.

In some examples, system 20 further comprises a plurality of magnetic-field-generating coils 42 and another generator 41. As generator 41 passes electric currents through coils 42, the coils generate a magnetic field. This magnetic field induces signals in electromagnetic sensors coupled to probe 22. The induced signals are carried through the probe to appropriate circuitry (including, for example, analog-to-digital conversion circuitry) in console 44. Processor 47 receives the signals from the circuitry and, based on the signals, computes the respective locations of the electromagnetic sensors (and hence, of the electrodes), e.g., as described in U.S. Pat. Nos. 5,391,199, 5,443,489, and 6,788,967 to Ben-Haim, in U.S. Pat. No. 6,690,963 to Ben-Haim et al., in U.S. Pat. No. 5,558,091 to Acker et al., and in U.S. Pat. No. 6,177,792 to Govari, whose respective disclosures are incorporated herein by reference.

Alternatively or additionally, system 20 may comprise multiple reference electrodes 49, which may be coupled to the subject's chest and/or back and connected to console 44 via wires running through a cable 39. In such examples, the processor may pass a current through each electrode 40 and measure the resulting voltages between the electrode and reference electrodes 49. Alternatively, the processor may apply a voltage between each electrode 40 and reference electrodes 49, and measure the resulting currents. Subsequently, the processor may compute the locations of electrodes 40 based on the measured voltages or currents. Such examples may utilize a location map calibrated using electromagnetic sensors, as described, for example, in U.S. Pat. No. 7,536,218 to Govari et al. and U.S. Pat. No. 8,456,182 to Bar-Tal et al., whose respective disclosures are incorporated herein by reference.

Alternatively, the processor may pass currents between reference electrodes 49 and measure the resulting voltages or currents at electrodes 40. Subsequently, the processor may compute the locations of electrodes 40 based on the measured voltages or currents, as described, for example, in U.S. Pat. No. 5,983,126 to Wittkampf and U.S. Pat. No. 5,944,022 to Nardella, whose respective disclosures are incorporated herein by reference.

In some examples, the probe further comprises a fluid-delivery tube configured to deliver an irrigating fluid from a pump, which is typically disposed in console 44, to the distal end of the probe, such that the irrigating fluid irrigates the blood of the subject.

Typically, system 20 further comprises a display 24, configured to display any relevant output. For example, display 24 may display an image or a model of heart 26 with an icon of the distal end of the probe, including spines 36, superimposed at the current location of the distal end.

Typically, switches 45a are further configured to connect each electrode to an analog-to-digital (A/D) converter, the output of which is received by the processor. The processor may thus measure the voltage between each electrode and a common reference, such as another electrode at the center of spines 36 or a Wilson's Central Terminal (WCT). Based on these voltages, the processor may calculate an electrogram voltage between any pair of electrodes 40. (Typically, immediately prior to a voltage being applied to an electrode by generator 43, the switches disconnect the electrode from the A/D converter.)

Following the IRE procedure, the physician withdraws the probe and/or advances the sheath until the spines collapse upon entering the sheath.

Is noted that probe 22 may be used not only for IRE but also for other types of procedures, such as diagnostic procedures or other types of ablation procedures. To facilitate these other types of procedures, generator 43 may be configured to apply any suitable voltage waveform, such as a radiofrequency voltage. It is further noted that probe 22 may be used even without the shorting functionality of wiring 45 as described herein.

In general, processor 47 may be embodied as a single processor, or as a cooperatively networked or clustered set of processors. The functionality of processor 47 may be implemented solely in hardware, e.g., using one or more fixed-function or general-purpose integrated circuits, Application-Specific Integrated Circuits (ASICs), and/or Field-Programmable Gate Arrays (FPGAs). Alternatively, this functionality may be implemented at least partly in software. For example, processor 47 may be embodied as a programmed processor comprising, for example, a central processing unit (CPU) and/or a Graphics Processing Unit (GPU). Program code, including software programs, and/or data may be loaded for execution and processing by the CPU and/or GPU. The program code and/or data may be downloaded to the processor in electronic form, over a network, for example. Alternatively or additionally, the program code and/or data may be provided and/or stored on non-transitory tangible media, such as magnetic, optical, or electronic memory. Such program code and/or data, when provided to the processor, produce a machine or special-purpose computer, configured to perform the tasks described herein.

Figure 2:
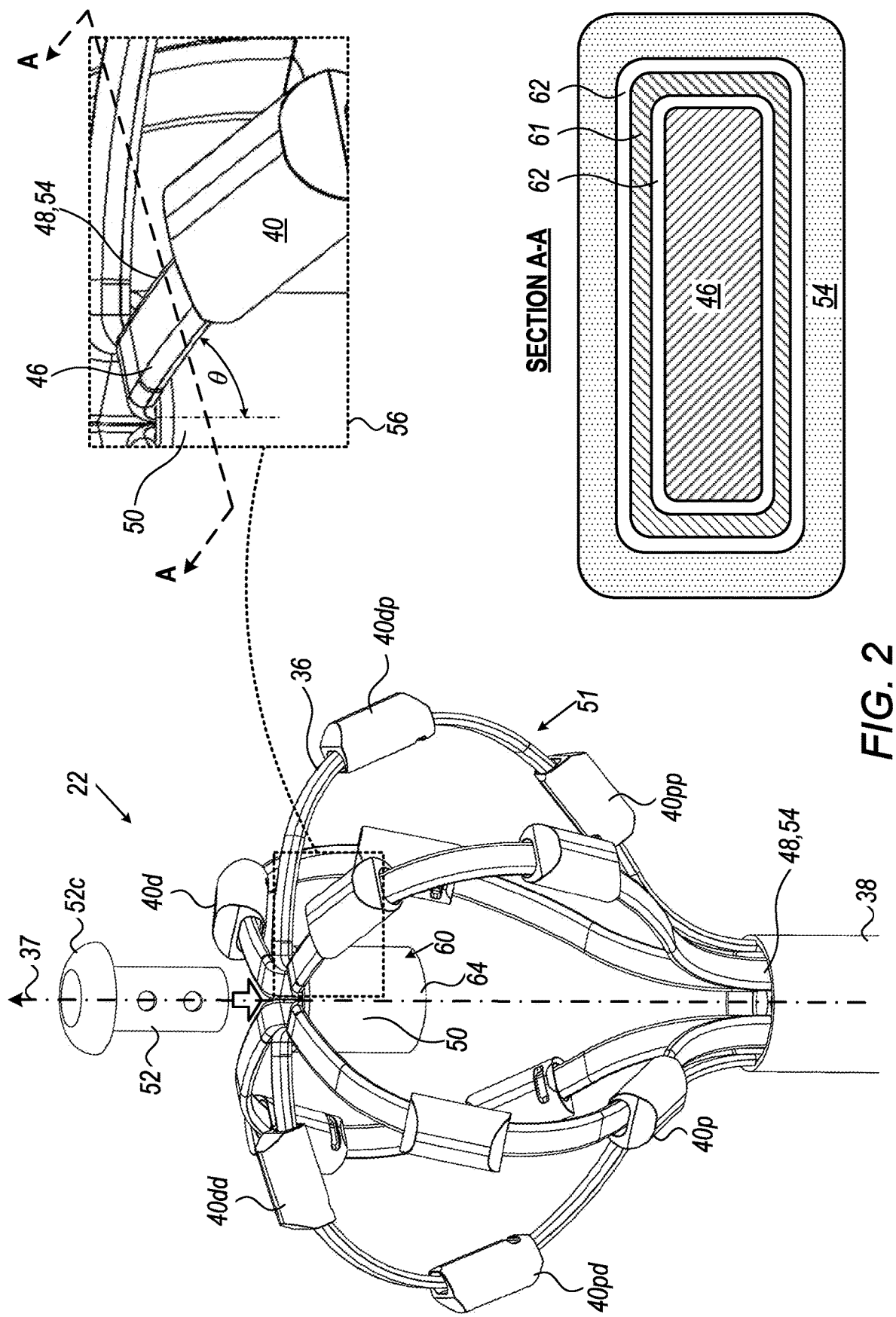
FIGS. 2-3 are schematic illustrations of an intrabody probe, in accordance with some examples of the present disclosure.

Reference is now made to FIG. 2, which is a schematic illustration of probe 22, in accordance with some examples of the present disclosure.

As shown in FIG. 2 (and also in FIG. 3, which is described below), spines 36 define a basket 51 at the distal end of probe 22. A longitudinal axis 37 of the probe extends distally from coupling element 38 (or directly from tube 34 (FIG. 1)) and passes through basket 51, such that electrodes 40 are spaced radially from longitudinal axis 37.

In some examples, probe 22 further comprises a support element 50. Spines 36 further comprise respective polymeric elements 48 extending from the distal ends of superelastic elements 46 and coupled to a surface 60 of support element 50 by virtue of being bent proximally, into alignment with surface 60, at the distal end of the support element. Polymeric elements 48 may be made of polyethylene terephthalate (PET) and/or any other suitable polymer.

By virtue of their flexibility, polymeric elements 48 facilitate the collapsing of the spines. In particular, as the spines collapse, the angle θ of each bend may decrease to less than 20 degrees, e.g., less than 10 degrees, which is generally smaller than the minimum bend angle achievable by superelastic elements 46.

Typically, polymeric elements 48 comprise respective sleeves 54, which cover superelastic elements 46 (e.g., by virtue of being shrink-wrapped around the superelastic elements) at least at respective distal ends of the superelastic elements, as shown in an inset portion 56 of FIG. 2. (The sleeve 54 in inset portion 56 is rendered transparent so as to expose the superelastic element 46 underneath.) Typically, electrodes 40 are coupled to the sleeves, such that the sleeves insulate the superelastic elements from the electrodes.

In some examples, superelastic elements 46 are entirely, or almost entirely, covered by sleeves 54. In such examples, the proximal ends of sleeves 54 may be coupled to coupling element 38 (e.g., to the inner surface of coupling element 38) or directly to tube 34 (FIG. 1).

In some examples, the wires connecting the electrodes to generator 43 (FIG. 1) pass through sleeves 54.

In some examples, probe 22 further comprises another polymer 61, such as ultra-high-molecular-weight polyethylene (UHMWPE) or a liquid crystal polymer (LCP), disposed between sleeves 54 and superelastic elements 46. (Typically, in such examples, polymer 61 comprises multiple filaments.) Typically, polymer 61 is coupled to sleeves 54 and to superelastic elements 46 by an epoxy 62. Advantageously, polymer 61 may help inhibit elongation of sleeves 54.

Typically, support element 50 comprises a supporting tube 64. Surface 60, to which polymeric elements 48 are coupled, is an inner surface of supporting tube 64. (Thus, polymeric elements 48 bend over the distal end of the supporting tube.) Typically, the longitudinal axis of supporting tube 64 is parallel to that of the distal end of tube 34 and/or coupling element 38.

In some examples, supporting tube 64 has a circular cross-section, i.e., the supporting tube is cylindrical. In other examples, the supporting tube has a polygonal cross-section. In such examples, the number of sides of the polygon is typically the same as the number of spines, such that each polymeric element 48 may be coupled to a different respective side. For example, for examples with six spines, the supporting tube may have a hexagonal cross-section.

In some examples, probe 22 further comprises a plug 52 that plugs supporting tube 64 so as to inhibit decoupling of the polymeric elements from the inner surface of the supporting tube. (Optionally, plug 52 may comprise a distal cap 52c that covers the distal surfaces of the polymeric elements near support element 50.) Alternatively or additionally, tube 64 may be filled with any suitable adhesive.

Any suitable number of electrodes, such as between one and four electrodes, may be coupled to each spine. For example, FIG. 2 shows an example in which two electrodes are coupled to each of six spines: a more distal, or "north," electrode 40d, and a more proximal, or "south," electrode 40p. To facilitate the collapsing of the spines, distal electrodes 40d that are opposite one another are slightly staggered with respect to one another, as are proximal electrodes 40p that are opposite one another. Thus, the probe comprises three distal electrodes 40dd, three opposing distal electrodes 40dp that are slightly proximal to distal electrodes 40dd, three proximal electrodes 40pd, and three opposing proximal electrodes 40pp that are slightly proximal to proximal electrodes 40pd.

Figure 3:
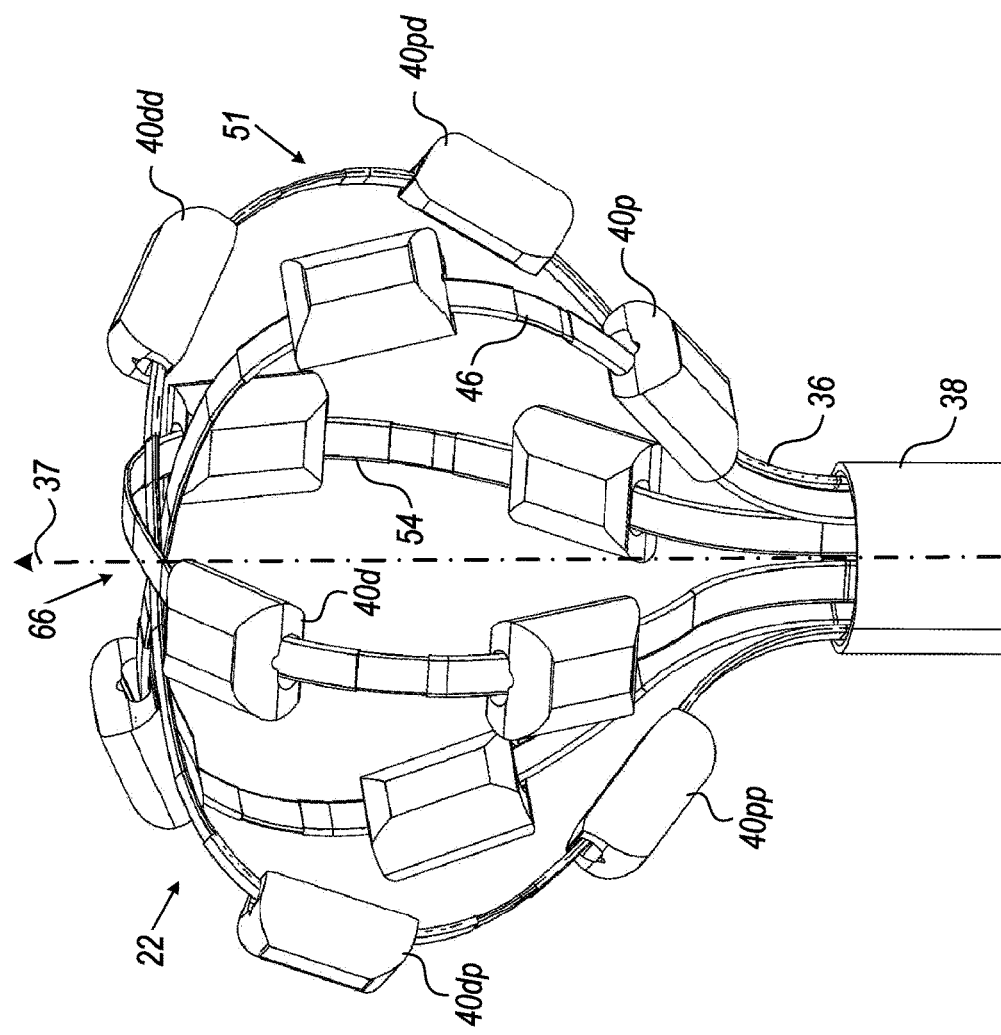

Reference is now made to FIG. 3, which is a schematic illustration of probe 22 in accordance with other examples of the present disclosure.

In some examples, the two ends of each spine 36 are coupled to coupling element 38 (or directly to tube 34) opposite one another, such that each spine is shaped to define a loop. Each superelastic element 46 is partially covered by a set of one or more polymeric sleeves 54, electrodes 40 being coupled to respective ones of the polymeric sleeves. The spines cross over each other at a distal crossover 66.

Probe 22 may comprise any suitable number of spines, such as between two and six (e.g., three) spines. Any suitable number of electrodes, such as between two and eight electrodes, may be coupled to each spine, typically such that half the electrodes are at each side of crossover 66. For example, FIG. 3 shows an example in which four electrodes are coupled to each spine: a proximal electrode 40pd and a distal electrode 40dd at one side of crossover 66, and, at the other side, a proximal electrode 40pp and a distal electrode 40dp, which are slightly offset proximally with respect to proximal electrode 40pd and distal electrode 40dd, respectively.

In some examples, each of the superelastic elements is covered by at least two polymeric sleeves and is uncovered between the two polymeric sleeves. Thus, each superelastic element may deliver additional current to the tissue, as further described below with reference to FIG. 5.

Advantageously, at least one of the superelastic elements is uncovered at crossover 66. Thus, the spines may assume a smaller collapsed profile, relative to if all the superelastic elements were covered at the crossover. In addition, by virtue of at least one of the superelastic elements being uncovered, similarly-positioned electrodes on different spines may be better aligned with each other. For example, each of distal electrodes 40dd may lie at approximately the same distance from tube 34, as may each of distal electrodes 40dp, each of proximal electrodes 40pd, and each of proximal electrodes 40pp.

Typically, the number of superelastic elements uncovered at crossover 66 is the maximum that is possible without risking a shorting of two spines to one another. For example, in examples in which no electrical current is passed through the spines, all the superelastic elements may be uncovered, as shown in FIG. 3. In other examples, every other superelastic element may be uncovered, such that no two superelastic elements touch one another. In other words, numbering the superelastic elements 1 . . . . M for M even, where the first superelastic element is most proximal at crossover 66 and the $M^{th}$ superelastic element is most distal, all the odd-numbered superelastic elements, or all the even-numbered superelastic elements, may be uncovered. For M odd, all the odd-numbered superelastic elements may be uncovered.

Typically, the wires connecting the electrodes to generator 43 (FIG. 1) run along the inner surface of the spines.

Wiring

Figure 4:
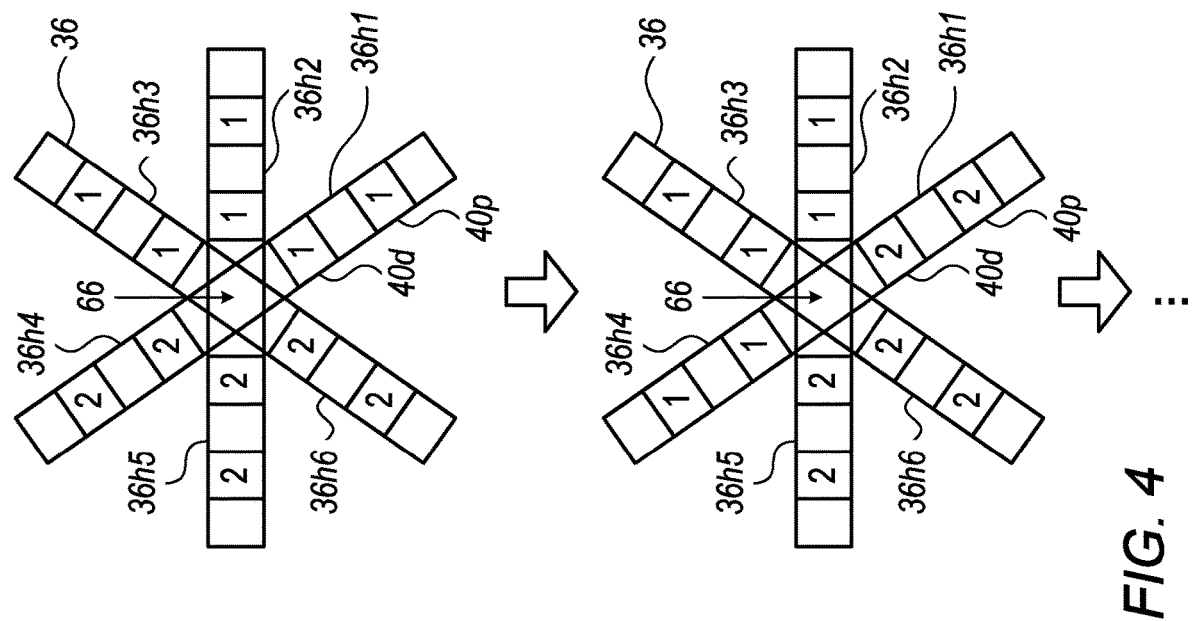
FIGS. 4-6 are schematic illustrations of schemas for wiring electrodes during an IRE procedure, in accordance with some examples of the present disclosure.

Reference is now made to FIG. 4, which is a schematic illustration of a schema for wiring electrodes 40 during an IRE procedure, in accordance with some examples of the present disclosure.

By way of introduction, it is noted that spines 36 typically comprise multiple half-spines 36h extending between tube 34 (e.g., via a coupling element) and the distal end of the probe. For example, in the example of FIG. 2, each spine is a half-spine, in that the spine does not define a loop, but rather, terminates at support element 50 (FIG. 2). As another example, in the example of FIG. 3 (also shown in FIG. 4), each spine comprises two half-spines continuous with one another at crossover 66.

FIG. 4 shows a view of spines 36 from the distal end of the probe, and identifies six half-spines 36h1, 36h2, 36h3, 36h4, 36h5, and 36h6. To facilitate the description that follows, each spine is shown in FIG. 4 as if the spine were decoupled from tube 34 (FIG. 1) and laid flat on a surface. Furthermore, for ease of illustration, the offset between distal electrodes 40dd and 40dp, and the offset between proximal electrodes 40pd and 40pp, are ignored.

In some examples, the first subset of electrodes shorted to each other by wiring 45 (FIG. 1) are coupled to one or more adjacent first ones of the half-spines, and the second subset of electrodes shorted to each other are coupled to one or more adjacent second ones of the half-spines.

Typically, in such examples, the first subset is coupled to N/2 of the half-spines and the second subset is coupled to the other N/2 of the half-spines, N being the number of half-spines. Thus, the first subset, which may be referred to as the "eastern" subset, are opposite the second subset, which may be referred to as the "western" subset. For example, as shown at the upper portion of FIG. 4, the first subset, each electrode of which is labeled by a "1," may be coupled to half-spines 36h1, 36h2, and 36h3, while the second subset, each electrode of which is labeled by a "2," may be coupled to half-spines 36h4, 36h5, and 36h6.

As described above with reference to FIG. 1, the shorting of the electrodes may be hardwired. Typically, however, processor 47, by controlling switches 45a (FIG. 1), rotates the electrodes during the IRE procedure.

For example, after a voltage is applied between the first and second subsets as shown at the upper portion of FIG. 4, the processor may cause the switches to connect the electrodes on half-spine 36h4 to the first subset, and the electrodes on half-spine 36h1 to the second subset, as shown at the lower portion of FIG. 4. Subsequently, the voltage may be applied again. The processor may then continue iterating through the settings of the switches, causing the generator to apply a voltage in each of the settings.

For example, Table 1 below shows a sequence of settings through which the processor may iterate (e.g., repeatedly). The entry in Table 1 corresponding to each half-spine and setting indicates the subset to which the electrodes on the half-spine belong per the setting. (It is noted that Setting 1 of Table 1 is shown at the upper portion of FIG. 4, while Setting 2 is shown at the lower portion of FIG. 4.)

TABLE 1

| | Setting 1 | Setting 2 | Setting 3 | Setting 4 | Setting 5 | Setting 6 |
| --- | --- | --- | --- | --- | --- | --- |
| 36h1 | 1 | 2 | 2 | 2 | 1 | 1 |
| 36h2 | 1 | 1 | 2 | 2 | 2 | 1 |
| 36h3 | 1 | 1 | 1 | 2 | 2 | 2 |
| 36h4 | 2 | 1 | 1 | 1 | 2 | 2 |
| 36h5 | 2 | 2 | 1 | 1 | 1 | 2 |
| 36h6 | 2 | 2 | 2 | 1 | 1 | 1 |

Figure 5:
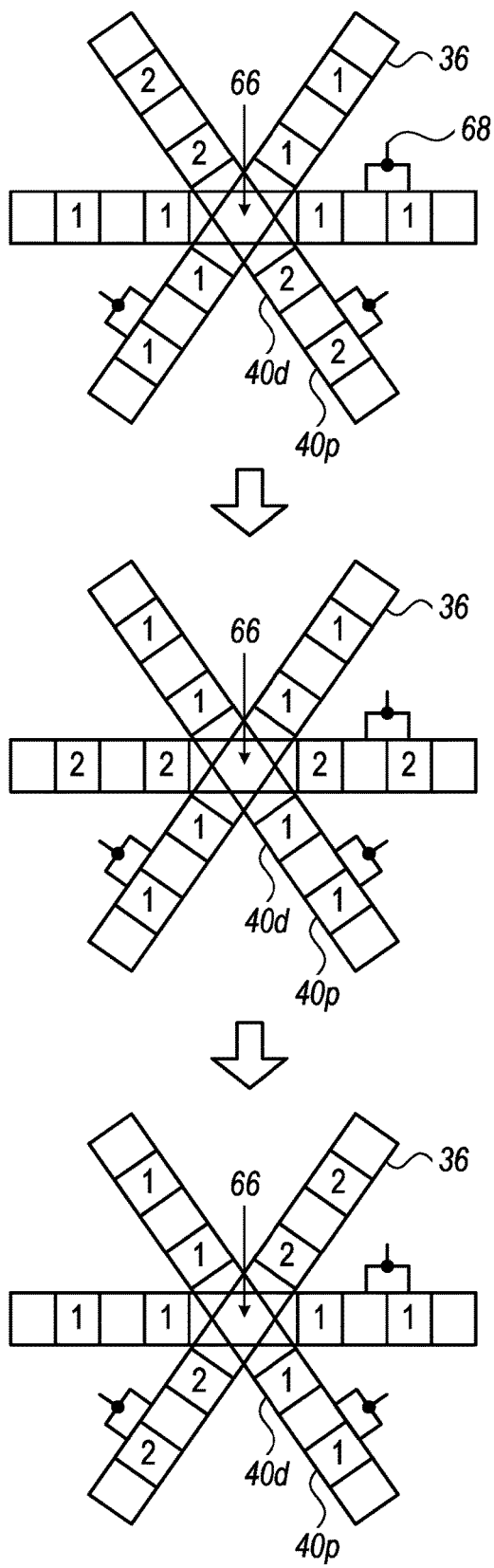

Reference is now made to FIG. 5, which is a schematic illustration of another schema for wiring electrodes 40, in accordance with some examples of the present disclosure.

In some examples, the first subset of electrodes are shorted to those of the spines to which the first subset are coupled, and the second subset are shorted to those of the spines to which the second subset are coupled. For example, the electrodes on each spine may be shorted to the superelastic element 46 (FIGS. 2-3) to which the electrodes are coupled. (The shorting of the electrodes to the spines is indicated in FIG. 5 by shorting symbols 68.)

Typically, in such examples, assuming M spines, the first subset includes those of the electrodes coupled to M/2 (or (M+1)/2, for M odd) of the spines, and the second subset includes those of the electrodes coupled to the other M/2 (or (M−1)/2, for M odd) of the spines.

Typically, processor 47 controls switches 45a (FIG. 1) so as to vary the first and second subsets. For example, for an example with three spines, the processor may iterate (e.g., repeatedly) through the three settings shown in FIG. 5.

Figure 6:
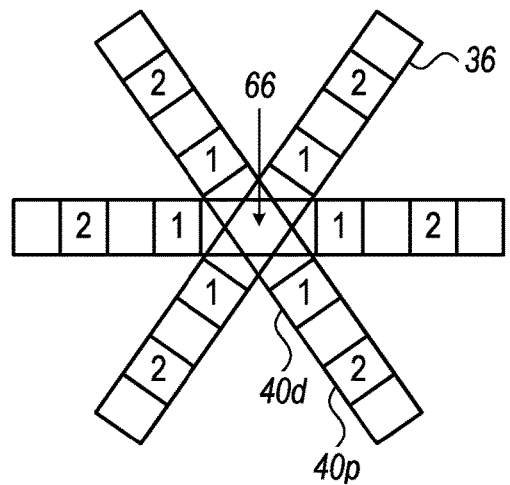

Reference is now made to FIG. 6, which is a schematic illustration of another schema for wiring electrodes 40, in accordance with some examples of the present disclosure.

In some examples, the first subset are distal to the second subset. For example, for examples with two electrodes coupled to each half-spine, the first subset may include distal electrodes 40d, and the second subset may include proximal electrodes 40p.

It is noted that at least two of the schemas of FIGS. 4-6 may be combined with each other, i.e., the processor may iterate (e.g., repeatedly) through a sequence of settings from multiple different schemas. For example, following the six settings of Table 1, the processor may iterate through the three settings of FIG. 5, and then the setting of FIG. 6.

It is emphasized that although FIGS. 4-6 show the example of FIG. 3 by way of example, the shorting of electrodes as described herein may be implemented with any suitable probe, such as the example of FIG. 2.

EXAMPLES

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus (22) including a tube (34), a support element (50), multiple spines (36) proximally coupled to the tube (34) and including respective expandable superelastic elements (46) and respective polymeric elements (48) extending from respective distal ends of the superelastic elements (46) and coupled to a surface (60) of the support element (50) by virtue of being bent proximally, into alignment with the surface (60), at a distal end of the support element (50), and multiple electrodes (40) coupled to the spines (36).

Example 2

The apparatus (22) according to Example 1, wherein the polymeric elements (48) include respective sleeves (54) covering the superelastic elements (46) at least at the distal ends of the superelastic elements (46).

Example 3

The apparatus (22) according to Example 2, wherein the sleeves (54) are shrink-wrapped around the superelastic elements (46).

Example 4

The apparatus (22) according to any one of Examples 2-3, wherein the electrodes (40) are coupled to the sleeves (54), such that the sleeves (54) insulate the superelastic elements (46) from the electrodes (40).

Example 5

The apparatus (22) according to any one of Examples 2-4, wherein respective proximal ends of the sleeves (54) are coupled to the tube (34).

Example 6

The apparatus (22) according to any one of Examples 2-5, wherein the sleeves (54) are made of a first polymer, and wherein the apparatus further includes a second polymer (61) disposed between the sleeves (54) and the superelastic elements (46).

Example 7

The apparatus (22) according to any one of Examples 1-6, wherein the support element (50) includes a supporting tube (64), and wherein the surface (60) is an inner surface of the supporting tube (64).

Example 8

The apparatus (22) according to Example 7, further including a plug (52) that plugs the supporting tube (64) so as to inhibit decoupling of the polymeric elements (48) from the inner surface.

Example 9

A method including deploying a probe from a sheath within a body of a subject, the probe including a tube, a support element, and multiple spines proximally coupled to the tube. The spines include respective expandable superelastic elements, and respective polymeric elements extending from respective distal ends of the superelastic elements and coupled to a surface of the support element by virtue of being bent proximally, into alignment with the surface, at a distal end of the support element. The method further includes, using multiple electrodes coupled to the spines, performing a procedure on the subject.

Example 10

An apparatus (22) including a tube (34) and multiple spines (36), each of the spines (36) having two ends coupled to the tube (34) opposite one another such that the spines (36) arc distally from the tube (34) and cross over each other at a crossover (66). The spines (36) include respective expandable superelastic elements (46) and respective sets of one or more polymeric sleeves (54) partially covering the superelastic elements (46) such that at least one of the superelastic elements (46) is uncovered at the crossover (66). The apparatus (22) further includes multiple electrodes (44) coupled to respective ones of the polymeric sleeves (54).

Example 11

The apparatus (22) according to Example 10, wherein at least half of the superelastic elements (46) are uncovered at the crossover (66).

Example 12

The apparatus (22) according to any one of Examples 10-11, wherein each of the superelastic elements (46) is covered by at least two of the polymeric sleeves (54) and is uncovered between the two of the polymeric sleeves (54).

Example 13

A method including deploying a probe from a sheath within a body of a subject, the probe including a tube and multiple spines. Each of the spines has two ends coupled to the tube opposite one another such that the spines arc distally from the tube and cross over each other at a crossover. The spines include respective expandable superelastic elements, and respective sets of one or more polymeric sleeves partially covering the superelastic elements such that at least one of the superelastic elements is uncovered at the crossover. The method further includes, using multiple electrodes coupled to respective ones of the polymeric sleeves, performing a procedure on the subject.

Example 14

A system (20) for use with multiple electrodes (40) coupled to respective spines (36) of a probe (22), the system (20) including multiple switches (45*a*) connected to the electrodes (40) and configured to short different respective first subsets of the electrodes (40) to each other and different respective second subsets of the electrodes (40) to each other per different respective settings of the switches (45*a*). The system (20) further includes a processor (47) configured to control the switches (45*a*) so as to alternate through the settings and, for each of the settings, cause a power generator (43) to apply a voltage between the shorted first subset and the shorted second subset while the probe (22) is deployed within a body of a subject (28).

Example 15

The system (20) according to Example 14, wherein the voltage has a constant positive amplitude for at least 100 ns and a constant negative amplitude for at least 100 ns.

Example 16

The system (20) according to Example 15, wherein the positive amplitude and negative amplitude have the same magnitude.

Example 17

The system (20) according to any one of Examples 14-16, wherein the spines (36) include multiple half-spines extending between a tube (34) and a distal end of the probe (22), and wherein, per at least one of the settings, the first subset of the electrodes (40) are coupled to one or more adjacent first ones of the half-spines, and the second subset of the electrodes (40) are coupled to one or more adjacent second ones of the half-spines.

Example 18

The system (20) according to Example 17, wherein the half-spines consist of N half-spines, and wherein the first subset are coupled to N/2 of the half-spines and the second subset are coupled to another N/2 of the half-spines.

Example 19

The system (20) according to any one of Examples 14-18, wherein, per at least one of the settings, the switches (45*a*) short the first subset to those of the spines (36) to which the first subset are coupled, and short the second subset to those of the spines (36) to which the second subset are coupled.

Example 20

The system (20) according to any one of Examples 14-19, wherein, per at least one of the settings, the first subset are distal to the second subset.

Example 21

A method for use with multiple electrodes coupled to respective spines of a probe, the method including, by controlling multiple switches connected to the electrodes, causing the switches to short different respective first subsets of the electrodes to each other and different respective second subsets of the electrodes to each other per different respective settings of the switches. The method further includes, for each of the settings, causing a power generator to apply a voltage between the shorted first subset and the shorted second subset while the probe is deployed within a body of a subject.

Example 22

A computer software product for use with multiple electrodes (40) coupled to respective spines (36) of a probe (22), the computer software product comprising a tangible non-transitory computer-readable medium in which program instructions are stored, which instructions, when read by a processor (47), cause the processor (47) to control multiple switches (45*a*) connected to the electrodes (40) so as to cause the switches (45*a*) to short different respective first subsets of the electrodes (40) to each other and different respective second subsets of the electrodes (40) to each other per different respective settings of the switches (45*a*). The instructions further cause the processor (47) to cause a power generator (43), for each of the settings, to apply a voltage between the shorted first subset and the shorted second subset while the probe (22) is deployed within a body of a subject (28).

Example 23

The computer software product according to Example 22, wherein the voltage has a constant positive amplitude for at least 100 ns and a constant negative amplitude for at least 100 ns.

Example 24

The computer software product according to Example 23, wherein the positive amplitude and negative amplitude have the same magnitude.

Example 25

The computer software product according to any one of Examples 22-24, wherein the spines (36) include multiple half-spines extending between a tube (34) and a distal end of the probe (22), and wherein, per at least one of the settings, the first subset of the electrodes (40) are coupled to one or more adjacent first ones of the half-spines, and the second subset of the electrodes (40) are coupled to one or more adjacent second ones of the half-spines.

Example 26

The computer software product according to Example 25, wherein the half-spines consist of N half-spines, and wherein the first subset are coupled to N/2 of the half-spines and the second subset are coupled to another N/2 of the half-spines.

Example 27

The computer software product according to any one of Examples 22-26, wherein, per at least one of the settings, the first subset are shorted to those of the spines (36) to which the first subset are coupled, and the second subset are shorted to those of the spines (36) to which the second subset are coupled.

Example 28

The computer software product according to any one of Examples 22-27, wherein, per at least one of the settings, the first subset are distal to the second subset.

Example 29

A system for use with multiple electrodes coupled to respective spines of a probe, the system including wiring connected to the electrodes and configured to short at least one first subset of the electrodes to each other and at least one second subset of the electrodes to each other while the probe is deployed within a body of a subject. The system further includes a power generator, configured to apply a voltage between the shorted first subset and the shorted second subset, the voltage having a constant positive amplitude for at least 100 ns and a constant negative amplitude for at least 100 ns.

It will be appreciated by persons skilled in the art that the present disclosure is not limited to what has been particularly shown and described hereinabove. Rather, the scope of the present disclosure includes both combinations and subcombinations of the various features described hereinabove, as well as variations and modifications thereof that are not in the prior art, which would occur to persons skilled in the art upon reading the foregoing description. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A system for use with multiple electrodes coupled to respective spines of a probe, the system comprising:
    multiple switches connected to the electrodes and configured to short different respective first subsets of the electrodes to each other and different respective second subsets of the electrodes to each other per different respective settings of the switches; and
    a processor, configured to:
        control the switches so as to alternate through the settings;
        for each of the settings, cause a power generator to apply a voltage between the shorted first subset of the electrodes and the shorted second subset of the electrodes; and
        in at least one of the settings, cause the switches to short at least one respective first subset of the electrodes or one respective second subset of the electrodes to the spines to which the respective first subset of the electrodes or the respective second subset of the electrodes are coupled.

2. The system according to claim 1, wherein the voltage has a constant positive amplitude for at least 100 ns and a constant negative amplitude for at least 100 ns.

3. The system according to claim 2, wherein the positive amplitude and negative amplitude have the same magnitude.

4. The system according to claim 1,
    wherein the spines include multiple half-spines extending between a tube and a distal end of the probe, and
    wherein, per at least one of the settings, one or more electrodes in the first subset of the electrodes provided on a first set of adjacent half-spines are coupled to one another, and one or more electrodes in the second subset of the electrodes provided on a second set of adjacent half-spines are coupled to one another.

5. The system according to claim 4, wherein the half-spines consist of N half-spines, wherein N includes an even integer of at least two or more, and wherein the first subset of the electrodes is coupled to N/2 of the half-spines and the second subset of the electrodes is coupled to another N/2 of the half-spines.

6. The system according to claim 1, wherein the processor, in at least one of the settings, causes the switches to short the first subset of the electrodes to the spines to which the first subset of the electrodes is coupled, and short the second subset of the electrodes to the spines to which the second subset of the electrodes is coupled.

7. The system according to claim 1, wherein, per at least one of the settings, the first subset of the electrodes is distal to the second subset of the electrodes.

8. A method for use with multiple electrodes coupled to respective spines of a probe, the method comprising:
    by controlling multiple switches connected to the electrodes, causing the switches to short different respective first subsets of the electrodes to each other and different respective second subsets of the electrodes to each other per different respective settings of the switches;
    for each of the settings, causing a power generator to apply a voltage between the shorted first subset of the electrodes and the shorted second subset of the electrodes; and
    causing the switches to short at least one respective first subset of the electrodes or one respective second subset of the electrodes to the spines to which the respective first subset of the electrodes or the respective second subset of the electrodes are coupled.

9. The method according to claim 8, wherein the voltage has a constant positive amplitude for at least 100 ns and a constant negative amplitude for at least 100 ns.

10. The method according to claim 8,
    wherein the spines include multiple half-spines extending between a tube and a distal end of the probe, and
    wherein, per at least one of the settings, one or more electrodes in the first subset of the electrodes provided on a first set of adjacent half-spines are coupled to one another, and one or more electrodes in the second subset of the electrodes provided on a second set of adjacent half-spines are coupled to one another.

11. The method according to claim 10, wherein the half-spines consist of N half-spines, wherein N comprises an even integer of at least two or more, and wherein the first subset of the electrodes is coupled to N/2 of the half-spines and the second subset of the electrodes is coupled to another N/2 of the half-spines.

12. The method according to claim 8, further comprising, in at least one of the settings, causing the switches to short the first subset of the electrodes to the spines to which the first subset of the electrodes is coupled, and short the second subset of the electrodes to the spines to which the second subset of the electrodes is coupled.

13. The method according to claim 8, wherein, per at least one of the settings, the first subset of the electrodes is distal to the second subset of the electrodes.

14. A computer software product for use with multiple electrodes coupled to respective spines of a probe, the computer software product comprising a tangible non-transitory computer-readable medium in which program instructions are stored, which instructions, when read by a processor, cause the processor to:
control multiple switches connected to the electrodes so as to cause the switches to short different respective first subsets of the electrodes to each other and different respective second subsets of the electrodes to each other per different respective settings of the switches, and for each of the settings, cause a power generator to apply a voltage between the shorted first subset of the electrodes and the shorted second subset of the electrodes; and
in at least one of the settings, cause the switches to short at least one respective first subset of the electrodes or one respective second subset of the electrodes to the spines to which the respective first subset of the electrodes or the respective second subset of the electrodes are coupled.

15. The computer software product according to claim 14, wherein the voltage has a constant positive amplitude for at least 100 ns and a constant negative amplitude for at least 100 ns.

16. The computer software product according to claim 14, wherein the spines include multiple half-spines extending between a tube and a distal end of the probe, and
wherein, per at least one of the settings, one or more electrodes in the first subset of the electrodes provided on a first set of adjacent half-spines are coupled to one another, and one or more electrodes in the second subset of the electrodes provided on a second set of adjacent half-spines are coupled to one another.

17. The computer software product according to claim 16, wherein the half-spines consist of N half-spines, wherein N comprises an even integer of at least two or more, and wherein the first subset of the electrodes is coupled to N/2 of the half-spines and the second subset of the electrodes is coupled to another N/2 of the half-spines.

18. The computer software product according to claim 14, wherein, per at least one of the settings, the first subset of the electrodes is shorted to the spines to which the first subset of the electrodes is coupled, and the second subset of the electrodes is shorted to the spines to which the second subset of the electrodes is coupled.

19. The computer software product according to claim 14, wherein, per at least one of the settings, the first subset is distal to the second subset.

20. A system for use with multiple electrodes coupled to respective spines of a probe, the system comprising:
wiring connected to the electrodes and configured to short at least one first subset of the electrodes to each other and at least one second subset of the electrodes to each other, and wiring connected to the electrodes and configured to short at least one first subset of the electrodes to each other and at least one second subset of the electrodes to each other, and to short at least one respective first subset of the electrodes or one respective second subset of the electrodes to the spines to short at least one respective first subset of the electrodes or one respective second subset of the electrodes to the spines to which the respective first subset of the electrodes or the respective second subset of the electrodes are coupled; and
a power generator, configured to apply a voltage between the shorted first subset of the electrodes and the shorted second subset of the electrodes, the voltage having a constant positive amplitude for at least 100 ns and a constant negative amplitude for at least 100 ns.

* * * * *